July 31, 1956 T. E. MOTOSE Plant Pat. 1,500
ROSE PLANT
Filed Oct. 10, 1955
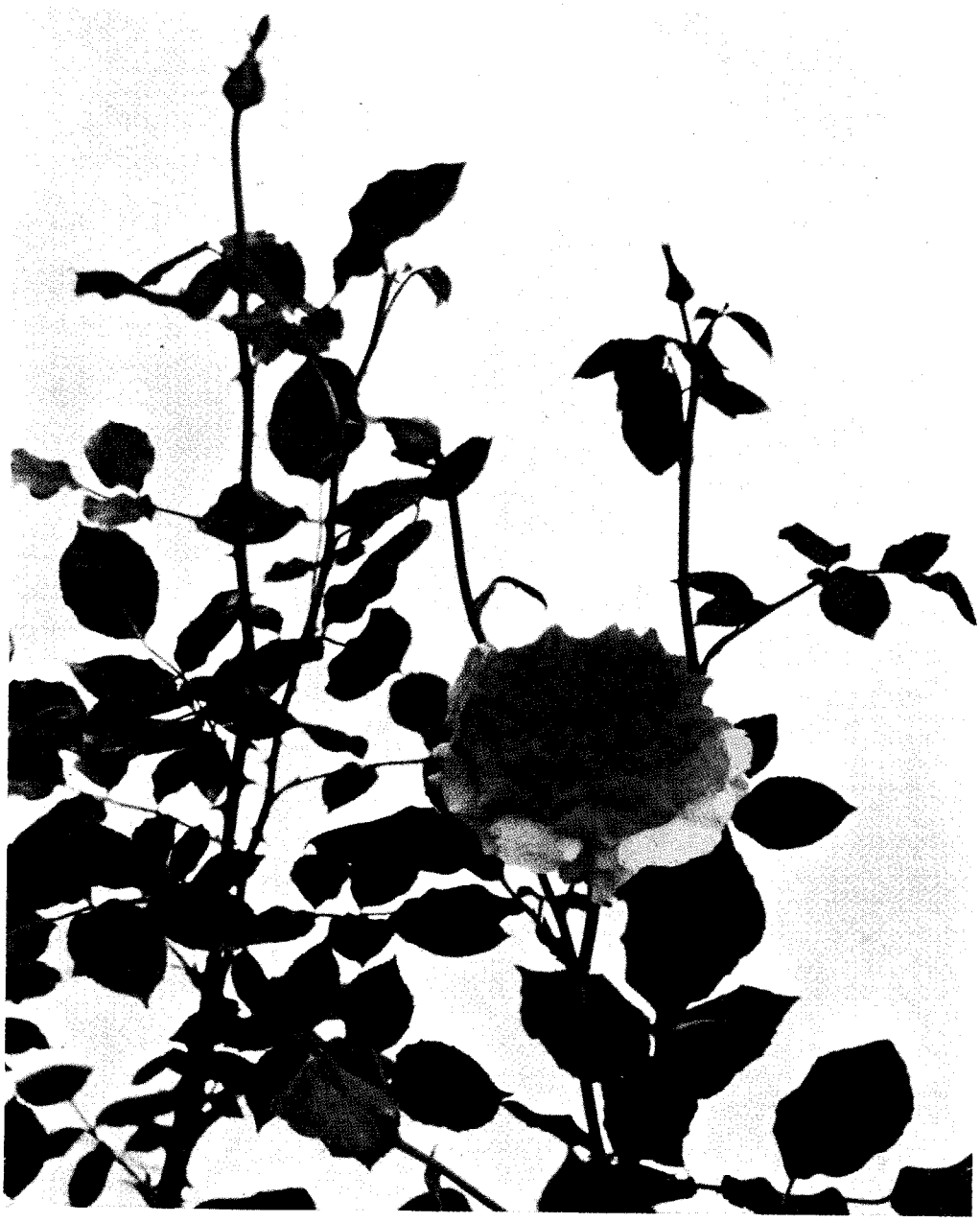
Inventor
Thomas Edison Motose United States Patent Office Plant Pat. 1,500
Patented July 31, 1956

1,500

ROSE PLANT

Thomas Edison Motose, Fairport, N. Y.

Application October 10, 1955, Serial No. 539,709

1 Claim. (Cl. 47—61)

This invention relates to a new and distinct variety of plant of the genus Rosa originated as a cross of the known variety Tawny Gold (Plant Patent No. 950) and a seedling (an unnamed cross of the known varieties Talisman (unpatented) and Tawny Gold).

In crossing Tawny Gold and the seedling, I had for my object the production of a rose possessing the strong fruity fragrance of Tawny Gold, the deep colorings found in Talisman seedlings and the hardiness and vigor of Talisman itself. After numerous trials the objective was attained.

This new variety possesses the following characteristics:

(*a*) Strong fruity fragrance resembling that of Tawny Gold;

(*b*) Smaller and thinner petals than those of its parents;

(*c*) Medium size blooms, but smaller than those of its parents;

(*d*) Intensity and distribution of orange and related colors in its bloom different from those of its parents and other roses;

(*e*) Floral form resembling that of Tawny Gold when partly opened, but different from those of Tawny Gold and Talisman when fully opened;

(*f*) Production of large quantity of medium size blooms almost endlessly during growing seasons in Fairport, N. Y., and regions of similar climate, until stopped by frost;

(*g*) Vigor of growth and Winter hardiness in New York State comparable to those of Talisman growing in the same region; and (*h*) Great resistance to the species and variety of fungus known as *Diplocarpon rosae,* as noticed in outdoor tests in Fairport, N. Y.

The combination of the above characteristics makes this variety new and distinct or different from its parents and all other known roses.

The above characteristics and the combination thereof of this new variety have been found to be established definitely and to hold true through succeeding asexual reproductions. Buddings, cuttings, layerages and graftings of the new variety done in Fairport, N. Y., greenhouse and outdoors, always confirmed the fact that the said characteristics and the combinations thereof are transmissible asexually.

The accompanying photograph of this new variety shows the shape, relative size and colors of the various parts of the plant. There is little or no differentiating feature in the very young leaves, in mature flower buds and very old woods.

The place where, and the time when, observations made for the specific purpose of compiling data for this specification: Fairport, N. Y., second week in September 1955.

The following is a detailed description of this new variety of rose plant, with color terminology in accordance to Ridgway's Color Standard and Nomenclature (when plate number is given with color name) or in accordance to the generally accepted meaning of Webster's standard dictionary (when no color plate number is given):

(1) PARENTAGE

A seedling originated as a cross of Tawny Gold (seed parent) and an unnamed seedling (pollen parent), the latter being a cross of Talisman and Tawny Gold.

(2) CLASSIFICATION

*Botanical.*— A shrub or woody perennial plant belonging to the continuous or recurrent blooming hybrid varieties of cultivated species of the genus Rosa.

*Commercial.*—A bush-type hybrid-tea rose plant.

(3) PLANT

*Form.*—Bushy and well branched.

*Growth.*—Very vigorous and fast growing.

*Height.*—Two and one-half feet to three feet outdoors in Fairport, N. Y., and frequently exceeding five feet in greenhouses.

(4) CANES AND STEMS

*Mature canes.*—Smooth bark, Lettuce Green (Plate 5) in color.

*Young canes.*—Smooth bark, Lettuce Green (Plate 5) in color.

*Very young canes.*—Smooth surface, Oil Green (Plate 5) overcast with Oxblood Red (Plate 1) in color.

*Very old canes.*—Slightly rough bark with brown colored streaks and areas.

(5) FOLIAGES

*Quantity.*—Abundant.

*Composition.*—Five to seven leaflets to an average leaf.

*Size.*—Medium.

*Shape.*—Oval pointed leaflets resembling in general pattern to those of its seed parent, except that they are smaller and the terminal leaflet is little more pointed.

*Texture.*—Both sides slightly leathery.

*Color.*—Both sides of very young leaves—Oil Green (Plate 5) with overcast of Oxblood Red (Plate 1); upper side of young leaves—Oil Green (Plate 5) with slight overcast of Oxblood Red (Plate 1); under side of young leaves—Yellowish Oil Green (Plate 5) with a slight overcast of Oxblood Red (Plate 1); upper side of mature leaves—Forest Green (Plate 17); under side of mature leaves—Light Bice Green (Plate 17).

*Serration.*—Multiple, small.

*Ribs and veins.*—Average hybrid tea markings, not conspicuous.

*Leaf stem.*—Bice Green (Plate 17) in color.

*Stipules.*—Light Bice Green (Plate 17) in color, medium in size.

(6) FLOWER BUD

*Size.*—Medium.

*Shape.*—Ovoid base and pointed upper tip.

*Sepals.*—Serrated and branched; Bice Green (Plate 17) outside and Biscay Green (Plate 17) inside.

*Calyx.*—Size—medium; shape—base half of sparrow's egg.

*Peduncle.*—Medium length, smooth, slender, strong, Bice Green (Plate 17) overcast with Oxblood Red (Plate 1).

*Color.*—Visible part of petals when sepals first divide—Bittersweet Orange (Plate 2) and frequently Orange (Plate 3); visible tips of inner petals after sepals divide—Grenadine (Plate 2); inside of visible petals when half opened—Grenadine (Plate 2); outer surface of petals when half opened—Bittersweet Orange (Plate 2); middle of partly opened bud viewed from above—Grenadine (Plate 2) overcast with Grenadine Red (Plate 2).

(7) FLOWER

*Opening.*—Opens up well in most weather conditions.

*Life span of bloom.*—Average hybrid tea rose bloom.

*Size.*—Medium, averaging four inches in diameter.

*Borne.*—Singly, rarely in multiple.

*Form.*—High centered when partly opened; does not flatten out into saucer shape.

*Color of bloom when about one-half to three-fourths opened as viewed from above.*—Bittersweet Orange (Plate 2) with an overcast of Grenadine (Plate 2).

*Colors of bloom when fully opened as viewed from above.*—Central area—Bittersweet Orange (Plate 2) with an overcast of Grenadine (Plate 2); intermediate area—Cadmium Orange (Plate 3); outer area—Pale Orange Yellow (Plate 3) overcast with Shrimp Pink (Plate 1), and frequently Maize Yellow (Plate 4) overcast with a trace of Shrimp Pink (Plate 1).

*General color as viewed from about ten feet away in good daylight.*—Bittersweet Orange (Plate 2) when partly opened and Cadmium Orange (Plate 3) when fully opened.

*Fragrance.*—Pleasant fruity fragrance resembling that of its seed parent.

*Discoloration.*—General coloring at the end of fourth day of bloom—Orange Buff (Plate 3) with an overcast of Shrimp Pink (Plate 1); general coloring at about the sixth day of bloom, Maize Yellow (Plate 4).

(8) PETALS

*Shape.*—Larger petals—oval with slightly pointed base; smaller and inner petals—ovate and irregular.

*Arrangement.*—Irregular.

*Persistence.*—Drops off cleanly.

*Thickness.*—Slightly thinner than those of the average hybrid tea roses.

*Appearance.*—Inside—satiny; outside—shiny.

*Texture.*—Smooth.

*Size.*—Smaller than those of its parents.

*Color of upper surface of outer petals when fully unfurled.*—Pale Orange Yellow (Plate 3) overcast with Shrimp Pink (Plate 1) and frequently Maize Yellow (Plate 4) overcast with light trace of Shrimp Pink (Plate 1).

*Color of under surface of outer petals when fully unfurled.*—Pale Orange Yellow (Plate 3).

*Color of upper and under surfaces of intermediate petals when fully unfurled.*—Cadmium Orange (Plate 3).

*Color of upper surface of inner petals and petalets when flower is fully or almost fully opened.*—Bittersweet Orange (Plate 2) with an overcast of Grenadine (Plate 2).

*Color of under surface of inner petals and petalets.*—Cadmium Orange (Plate 3) when bloom is fully opened.

*Color of base of petals (large and small).*—Orange Yellow (Plate 3) gradually merging into Lemon Chrome (Plate 4) towards the point.

*Number of petals.*—35 to 45 (average bloom).

(9) THORNS

*Size.*—Medium.

*Quantity.*—Ordinary.

*Shape.*—Narrow base, free-end pointed slightly downward.

*Color.*—Light yellowish-green with a pink overcast when young, and various degrees of buff when old.

(10) GENITAL ORGANS

*Anthers.*—Medium in size, Orange Yellow (Plate 3) in color, medium in quantity.

*Filaments.*—Medium in length and Capucine Orange (Plate 3) in color.

*Pollens.*—Medium in quantity, Orange Yellow (Plate 3) in color.

*Styles.*—Thin, uneven in height, Capucine Orange (Plate 3) toward the base and Morocco Red (Plate 1) or closely related red toward the upper end.

*Stigmas.*—Medium in size, Morocco Red (Plate 1) or closely related red on the underside and rim, with a Martius Yellow (Plate 4) area close around the orifice.

(11) DISEASE RESISTANCE

This new variety is very resistant to the fungus *Diplocapon rosae* under normal weather condition of Fairport, N. Y.

(12) CELL STRUCTURE

*Chromosomes.*—Polyploid, similar to those of its parents.

I claim:

A new and distinct hybrid plant of the continuous or recurrent blooming variety of the cultivated species of the genus Rosa, commonly known as hybrid-tea rose plant, characterized as to novelty by the combination of unusual and attractive colors of its blooms, rich fruity fragrance of its flowers, its ability or tendency to produce large quantity of medium size blooms almost endlessly during the growing seasons, its great resistance to the fungus *Diplocarpon rosae* and its foliage and bush characteristics, substantially as shown and described.

No references cited.